United States Patent [19]

Henderson

[11] Patent Number: 5,638,174
[45] Date of Patent: Jun. 10, 1997

[54] FLUID SENSING APPARATUS WITH A ROTATABLE MEMBER UTILIZING DIFFERENT LENGTH LIGHT PIPES FOR ALTERNATELY TRANSMITTING A LIGHT BEAM

[75] Inventor: Thomas A. Henderson, Rochester, N.Y.

[73] Assignee: Xerox Corporation, Stamford, Conn.

[21] Appl. No.: 519,860

[22] Filed: Aug. 25, 1995

Related U.S. Application Data

[63] Continuation of Ser. No. 241,326, May 11, 1994, abandoned.

[51] Int. Cl.$^6$ .................................................. G01N 21/00
[52] U.S. Cl. ........................... 356/343; 356/73; 356/338; 356/436; 356/440; 356/441; 73/861.77
[58] Field of Search ........................... 356/427, 426, 356/436–437, 440, 336, 343, 73, 337–338, 441–442; 73/861.77

[56] References Cited

U.S. PATENT DOCUMENTS

| | | | |
|---|---|---|---|
| 1,964,784 | 7/1934 | Nelson et al. | 116/117 |
| 1,998,495 | 4/1935 | Faban | 116/117 |
| 2,147,309 | 2/1939 | Moore | 116/117 |
| 2,204,463 | 6/1940 | Allen | 73/861.77 |
| 2,599,201 | 6/1952 | Rubenstein et al. | 116/117 |
| 2,723,562 | 11/1955 | Lutz et al. | 73/861.77 |
| 3,217,539 | 11/1965 | Owen et al. | 73/861.77 |
| 3,776,817 | 12/1973 | Van Der Pfordten | 356/343 |
| 3,915,570 | 10/1975 | Skala | 356/343 |
| 4,013,953 | 3/1977 | Skala | 73/861.77 |
| 4,037,973 | 7/1977 | Carr | 356/206 |
| 4,101,874 | 7/1978 | Denison et al. | 340/606 |
| 4,193,694 | 3/1980 | Smith | 356/407 |
| 4,428,243 | 1/1984 | Taylor | 73/861.77 |
| 4,549,809 | 10/1985 | Minekane et al. | 356/436 |
| 4,571,995 | 2/1986 | Timme | 73/861.77 |
| 4,637,730 | 1/1987 | Ponstingl et al. | 356/411 |
| 4,745,877 | 5/1988 | Chang | 116/274 |
| 4,793,190 | 12/1988 | Chang | 73/861.33 |
| 4,981,362 | 1/1991 | deJong et al. | 356/436 |
| 5,192,972 | 3/1993 | Kroll et al. | 355/208 |

FOREIGN PATENT DOCUMENTS

| | | | |
|---|---|---|---|
| 0039244 | 11/1981 | European Pat. Off. | 73/861.77 |
| 2346217 | 3/1974 | Germany | 73/861.77 |
| 55-029780 | 3/1980 | Japan | 356/440 |

*Primary Examiner*—Frank Gonzalez
*Assistant Examiner*—Jason D. Vierra Eisenberg
*Attorney, Agent, or Firm*—Donald L. Webber

[57] ABSTRACT

A apparatus for sensing flow and/or other characteristics of a fluid, including an emitter adapted to project a light beam, a detector adapted to transmit a signal in response to receiving the light beam and a rotatable member for transmitting the beam of light from the emitter to the detector through a quantity of the fluid. Optic fibers/light pipes may be used to transmit light to the emitter from a light source, through the rotatable member and to a processor remote from the detector. The rotatable member may also include reflective and nonreflective zones for transmitting light passing through the fluid to the detector. A plurality of light pipes, blades, emitters and detectors may be used on the rotating member depending on a particular application of the present invention.

12 Claims, 7 Drawing Sheets

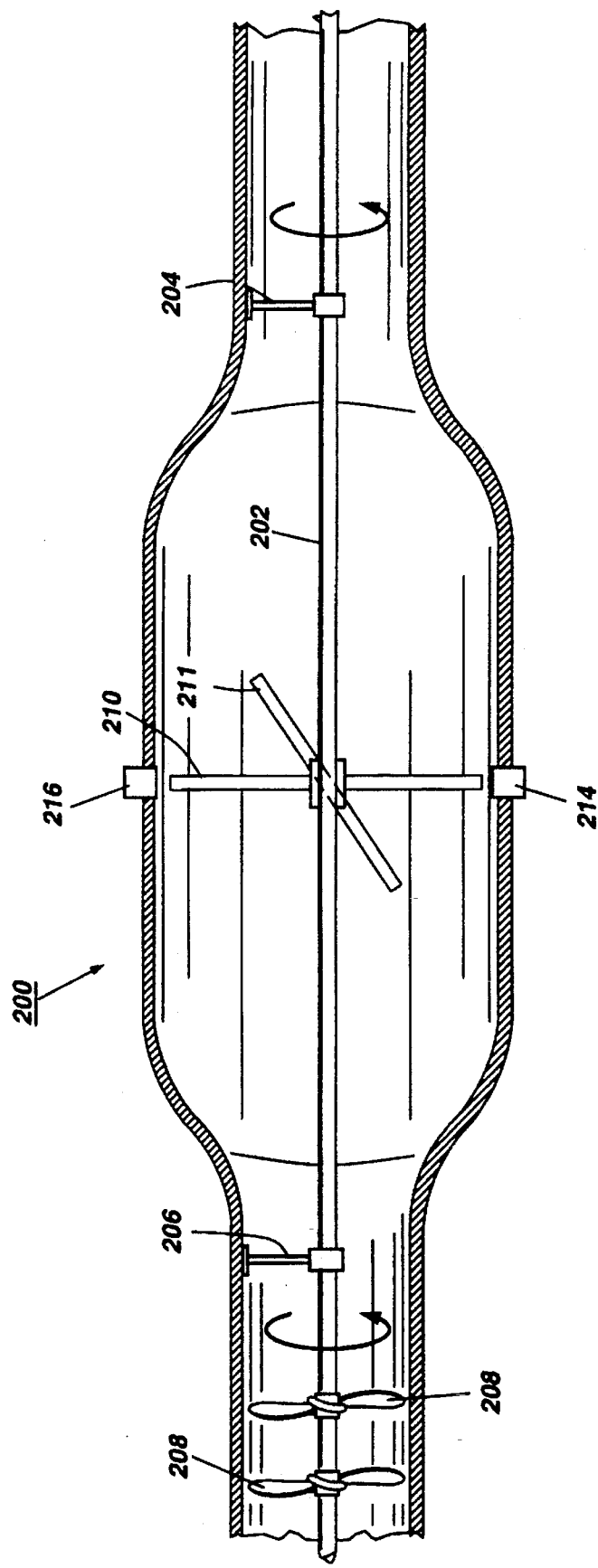

FLUID SENSING APPARATUS WITH A ROTATABLE MEMBER UTILIZING DIFFERENT LENGTH LIGHT PIPES FOR ALTERNATELY TRANSMITTING A LIGHT BEAM

This is a continuation of application Ser. No. 08/241,326, filed May 11, 1994, abandoned.

The present invention relates generally to fluid sensors that may be employed in a variety of devices to include copying and printing machines, and more particularly concerns optical sensors capable of determining fluid flow rates, density, particulate content, light transmittance, spectral attributes and/or other fluid characteristics.

In particular, systems involving fluid flows may require that a variety of components and parameters of those fluids be closely monitored. Arrays of various types of fluid sensors are being incorporated into a variety of technologically advanced machines; these sensors must be reliable and durable, so as to accurately monitor the requisite aspects of moving fluids in a variety of environments. Increased diagnostic, control and automation capabilities have also made it desirable to position reliable light emitter and receptor sensing systems in multiple locations in a flow path of a system. The connection of these emitters and receptors by power/data cables, optic fibers or other means to the remote data collection/analysis points can result cost savings, increased reliability and improved overall system performance.

For example, copying and printing machines using liquid inks, fuser oils or other fluids may require sensors to accurately sense and evaluate the density, particulate content, light transmittance, flow rates and other aspects of the liquids used. In such applications, a flowing material may be illuminated with a collimated beam of light emitted from a light emitter/optical fiber, preferably provided by an infrared LED (light emitting diode), or by variety of light sources. A portion of the light directed in this fashion at a fluid can pass through a portion of the fluid to a light detector or other sensor, so that flow speed and other fluid characteristics may be monitored.

Various sensors have been devised for sensing various fluid flow parameters and conditions, including those described in the following disclosures which appear to be relevant:

U.S. Pat. No. 5,119,132 Patentee: Kroll et al. Issued: Mar. 9, 1993

U.S. Pat. No. 4,981,362 Patentee: deJong et al. Issued: Jan. 1, 1991

U.S. Pat. No. 4,793,190 Patentee: Chang Issued: Dec. 27, 1988

U.S. Pat. No. 4,745,877 Patentee: Chang Issued: May 24, 1988

U.S. Pat. No. 4,637,730 Patentee: Ponstingl et al. Issued: Jan. 20, 1987

U.S. Pat. No. 4,193,694 Patentee: Smith Issued: Mar. 18, 1980

U.S. Pat. No. 4,101,874 Patentee: Denison et al. Issued: Jul. 18, 1978

U.S. Pat. No. 4,037,973 Patentee: Carr Issued: Jul. 26, 1977

U.S. Pat. No. 2,599,201 Patentee: Rubenstein, et al Issued: Jun. 3, 1952

U.S. Pat. No. 2,147,309 Patentee: Moore Issued: Feb. 14, 1939

U.S. Pat. No. 1,998,495 Patentee: Fagan Issued: Apr. 23, 1935

U.S. Pat. No. 1,964,784 Patentee: Nelson, et al Issued: Jul. 3, 1934

U.S. Pat. No. 5,119,132 discloses a toner monitor which is periodically caused to read a simulated nominal toner concentration. A difference between the monitored output and the expected toner concentration is applied to a compensation device. The simulated nominal toner concentration signal is obtained by periodic alignment of the toner monitor with a magnetically permeable member.

U.S. Pat. No. 4,981,362 discloses a method and apparatus for measuring the particle concentration in a fluid that is passed between a reciprocally movable window and a single photodetector. A collimated beam of light is directed through the window and fluid to the photodetector. The window is moved from a first predetermined location to a second predetermined location to vary the light beam path length, the ratio of the two signals provides the data needed to determine the particle concentration in the fluid. A rubber "O" ring around the cylinder seals the fluid inside the sensor. A single set of optics, detectors and amplifiers is used, so as to eliminate errors that may arise from a relative drift between two detectors.

U.S. Pat. No. 4,793,190 discloses a device for measuring and indicating fluid flow around a flow bend which includes a housing which is connected with the outer side of the curvature of the flow bend. There is a rotor with a number of substantially radial blades which is free to rotate about a fixed axis in the flow cavity. The hydrodynamics of the flow around the bend generates a secondary circulating flow in the cavity which induces a vortex flow; the vortex strength increases with the rate of the bend flow. The rotor, which is substantially co-axial with the vortex, is driven by the vortex to turn in the flow cavity. The rotating speed of the turning rotor is monitored by an electrical sensor which provides the flow rate measurement through a predetermined correlation. For sight flow indication application a view port is provided for visual observation of the rotor which provides a positive indication of fluid flow in the flow band.

U.S. Pat. No. 4,745,877 discloses a rotary sight flow indicator which provides a visual indication of fluid flow and of the flow direction by the rotation of a shrouded cross-flow rotor. The sight flow indicator consists of a housing with a cavity containing the rotor and its shroud, and at least one view window. The rotor comprises a number of radial blades attached to a rotatable shaft.

U.S. Pat. No. 4,637,730 discloses an optical absorptiometer which is characterized by a light source unit of a broad wavelength having a source of constant energy which is collimated into two light beams, one of which is transmitted through the liquid to be measured, and another beam which is transmitted through a conductor and acts as a reference beam, and a detector unit which contains two photocells, one photocell for measuring the beam transmitted through the liquid to be measured, and another photocell which measures the reference beam.

U.S. Pat. No. 4,193,694 discloses a color monitoring device is provided for measuring the concentration of a colored component in a flowing gas or liquid stream in which polychromatic light is passed through a frosted lens, then through a transparent sight tube through which the flowing stream passes. The light then passes through a second frosted lens, then through a sight mask which divides the light into two beams, one beam then passing through a first filter and the second beam passing through a second filter, the light beams passing through the filters then being directed to a first then second photoconductor.

U.S. Pat. No. 4,101,874 discloses a small diameter transparent visible fluid flow indicator suitable for mounting behind an opening in an instrument panel contains a six-bladed wheel which rotates according to the flow of fluid passing through orifices in the indicator housing. Each of the six blades of the wheel contains a small magnet oppositely polarized from the magnets in the adjacent blades to create alternate magnetic fields that pass through a pickup coil embedded in the housing which provides both a visible indication of fluid flow and also controls an alarm if the fluid flow stops or varies from some predetermined value.

U.S. Pat. No. 4,037,973 discloses a device for measuring particles in a liquid, utilizing a light source for the illumination of two detectors, one through a relatively short distance and the other through a relatively long distance. A reference signal produced by the first cell is supplied to an amplifier and indicator, and a measurement signal produced by the second detector is supplied to the amplifier and indicator. The two detectors and light source and contained in a small housing, remote from the amplifier and indicator.

U.S. Pat. No. 2,599,201 discloses a fluid flow indicator and more particularly an axial flow turbine oil line flow indicator. The indicator comprises generally a tubular casing encasing an elongated rotor or vane. The casing is formed with an integral inwardly directed radial flange for providing a stop for the rotor to prevent displacement thereof from the casing under the influence of fluid flow and is secured within suitable coupling members for facilitating the insertion of the indicator in a fluid flow line.

U.S. Pat. No. 2,147,309 discloses a flow indicating device and more particularly to that type of indicating device used in connection with gasoline pumps and commonly called a spinner. The present invention provides a flow indicator in which the indicating member will rotate at a substantially uniform speed regardless of the total amount of flow of the fluid through the discharge line so long as said total amount does not decrease below a predetermined minimum quantity.

U.S. Pat. No. 1,998,495 discloses a liquid flow indicator and more particularly a device for use with gasoline dispensing stations. The present invention in preferred form comprises the provision of a removable top carrying the top bearing for a vertical shaft of the indicator symbol and wherein the vertical shaft comprises a tubular member with one end terminating above the line of vision through the transparent chamber and the other end terminating in the line of flow of the gasoline in such manner as to provide an aspirating action through the tubular member which at all times withdraws the fluids from the upper end of the transparent chamber whereby the entrapment of air in the transparent chamber is completely avoided.

U.S. Pat. No. 1,964,784 discloses a device adapted to be interposed in a liquid circuit and containing an element which is rotatable by the moving liquid and visible through a transparent portion of a housing. More specifically, the invention is directed to a particular type of rotatable member which is devised to operate in coaxial relation to the liquid stream. The housing for this member is specially formed so that its removal may be accomplished without disturbing or dismantling the housing.

In accordance with one aspect of the present invention, there is provided an apparatus for sensing a fluid, including an emitter adapted to project a light beam, a detector adapted to transmit a signal in response to receiving the light beam and a rotatable member for transmitting the beam of light from the emitter to the detector through a quantity of the fluid.

Other aspects and features of the present invention will become apparent as the following description proceeds and upon reference to the drawings, in which:

FIG. 5 is an elevational view, partially in section, showing another embodiment of a sensor of the present invention;

Figure 1:
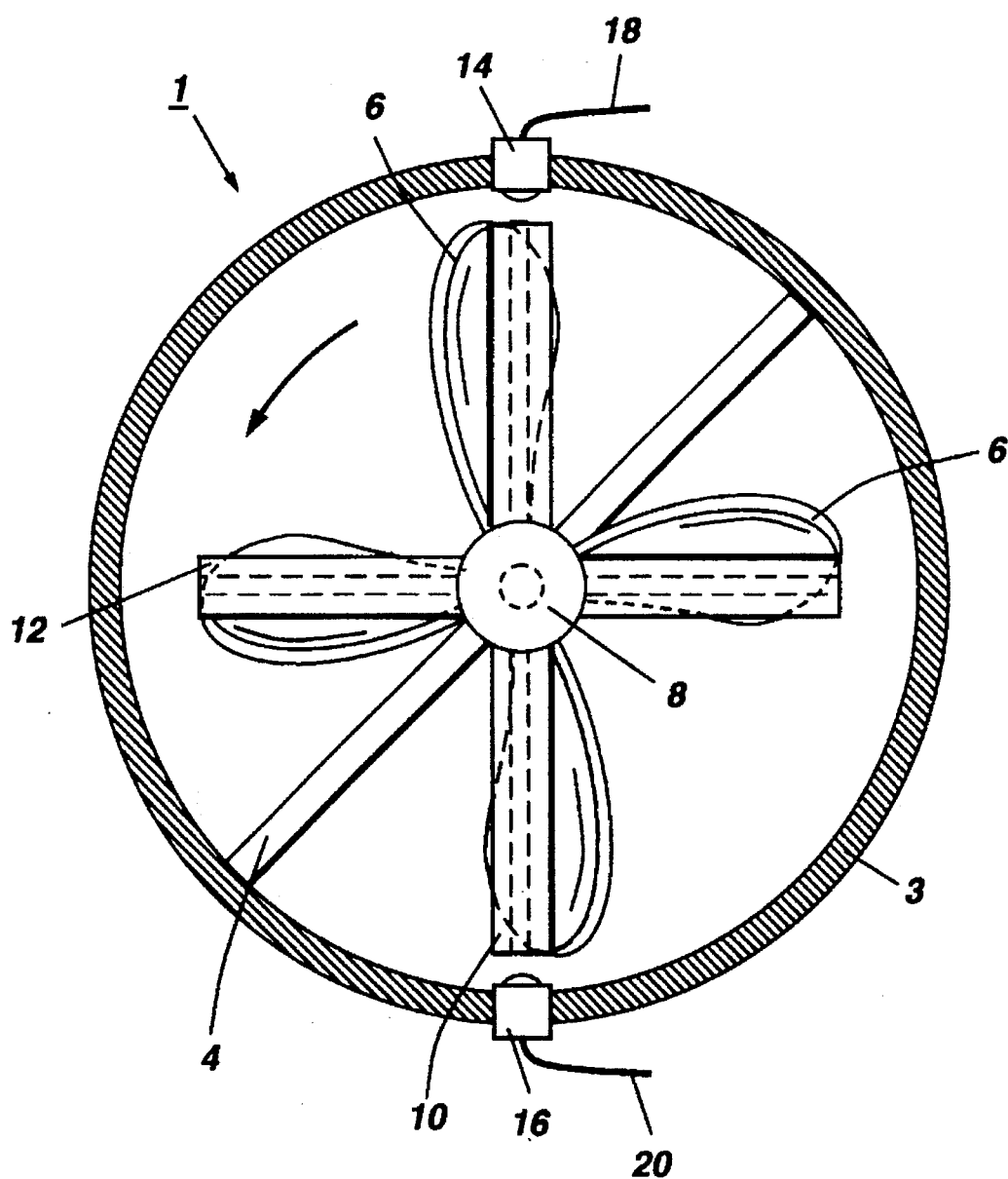
FIG. 1 is an elevational view, partially in section, showing a sensor arrangement in accordance with the present invention.

While the present invention will hereinafter be described in connection with preferred embodiments thereof, it will be understood that it is not intended to limit the invention to these embodiments. On the contrary, it is intended to cover all alternatives, modifications and equivalents, as may be included within the spirit and scope of the invention as defined by the appended claims.

For a general understanding of the features of the present invention, reference is made to the drawings. In the drawings, like reference numerals have been used throughout to identify identical elements.

FIG. 1 shows a cross sectional view of combined flow rate and fluid density sensor 1. Support member 4 is shown connected to flow tube 3 at two positions. A rotatably mounted member, prop 6, is mounted on axle 8. Axle 8 is rotatably attached to support 4, such that prop 6 turns freely according to fluid flow through blow tube 3. Light pipes 10 and 12 are formed within interior areas of prop 6, and pass through the blades or fins of prop 6 as shown. Emitter 14 emits light such that when light pipe 10 or 12 aligns with emitter 14 and detector 16, light is transmitted through the fluid across the gap between the light pipe ends. Alternatingly, light thereafter passes through each light pipe 10 or 12 and across the gaps at the ends of each light pipe and into detector 16. Light pipe 12 is shown in FIG. 1 as being slightly shorter than light pipe 10, such that when light pipe 12 is aligned with emitter 14 and detector 16, the light beam must pass through a greater fluid gap or distance than when light pipe 10 is aligned with emitter 12 and detector 16. In certain applications, it may be desirable to maintain uniform or laminar flow through tube 3. In other applications, fluid mixing according to movement of prop 6 may be desired.

As the fluid moves through flow tube 3, pressure on the blades of prop 6 causes prop 6 to rotate. As prop 6 rotates, the light pipes 10 and 12 will alternately align with emitter 14 and detector 16. The total fluid gap will be different in each case due to a difference in the length of light pipes 10 and 12. The sensed fluid gap includes the gaps at each end of each light pipe; thus, the total fluid gap is the length of the light pipe minus the distance between the source and detector. This two-gap system allows for some variation in the exact position of the light pipes while maintaining a constant total fluid gap, thus relaxing the tolerances on the bearing system for prop 6 while maintaining accurate measurement. As fluid flows through sensor 1, prop 6 is forced to rotate such that flow rate, density, particulate content and a variety of other fluid attributes may be detected, such as described in U.S. Pat. No. 4,981,363 to deJong et al., incorporated herein by reference. Prop 6 may be cast plastic, rubber, nylon, metal or other material affixed about the light pipes. Prop 6 may be fabricated of two halves or portions, and then coupled, heat cast or otherwise mated about light pipes 10 and 12. Alternatively, prop 6 may be cast from a translucent or transparent material and coated with a light-retaining material, so as to transmit light from emitter 14 to detector 16. Data/power lead 18 connects emitter 14 to remote power and/or data analysis devices (not shown); data and power lead 20 may likewise provide a signal from detector 16 (which may be a photosensor) to a processor, power source, data analysis sensor, controller or other device (not shown), such as described in U.S. Pat. No. 4,981,363 to deJong et al. or in U.S. Pat. No. 4,037,973 to Carr Fiber optic members (not shown in FIG. 1) may be used to transmit light from a remote light source to emitter 14 and from detector 16 to remotely positioned signal or light sensors/processors (also not shown in FIG. 1).

The concentration of absorbing and/or scattering particles in a fluid can be measured optically using a detector coupled with the sensors of the present invention using Beer's law; $T/T_0 = \exp(a \times c \times l)$, where "$T_0$" is the transmitted light intensity at zero concentration, "T" is the transmittance at the unknown concentration ("c"), "l" is the distance through the fluid that the transmitted light travels and "a" is the absorption coefficient. $T_0$ can be determined only once when continuous concentration sensing is conducted; light source intensity variations or other extraneous mechanisms and factors such as transmittance reduction, optical filming and others can cause erroneous measurements of concentration. The varied length, multi-light pipe/reflective area embodiments of the present invention can effectively employ such a single detector and amplifying circuit. In the embodiment of the present invention shown in FIG. 1, a single light source, emitter 14, illuminates two light pipes positioned so that the light travels through two different distances in the fluid. A single light detector provides all necessary data such that a comparison of the ratio of the two detected signals can eliminate $T_0$ from the equation, thus providing a signal that is relatively insensitive to light source intensity, accumulation of material on the optical surfaces and other factors. (Other embodiments of the present invention, such as those shown and described in conjunction with FIGS. 3A, 4A and 5–7, also can rely on intermittent use of single emitter and detector systems.) When two or more detectors are used (each with their own amplifier circuits), these detectors may drift with respect to each other and cause an error in the ratio of the transmittance.

FIG. 1 includes a movable prop 6 that requires no external electrical or other hook-ups to the emitter or detector to vary the fluid gaps. No mechanical fluid seals that may develop leaks over time are required, as flow tube 3 completely contain the fluid without the need for "O" rings or other such seals. In addition to measuring the concentration of light absorbing and/or scattering particles in a fluid, the embodiment shown in FIG. 1 also provides for flow measurement, according to the frequency of the intermittent passing of light from emitter 14 to detector 16 by light pipes 10 and 12. Again, a remote processor, controller or other device (not shown) can monitor for peaks in voltage caused by the various levels of transmitted light; each peak signal by detector 16 would correspond to light passing through one of the light pipes. Again, the frequency of the voltage peaks indicates how rapidly the wheel is turning so as to provide a measure of fluid flow.

Figure 2:
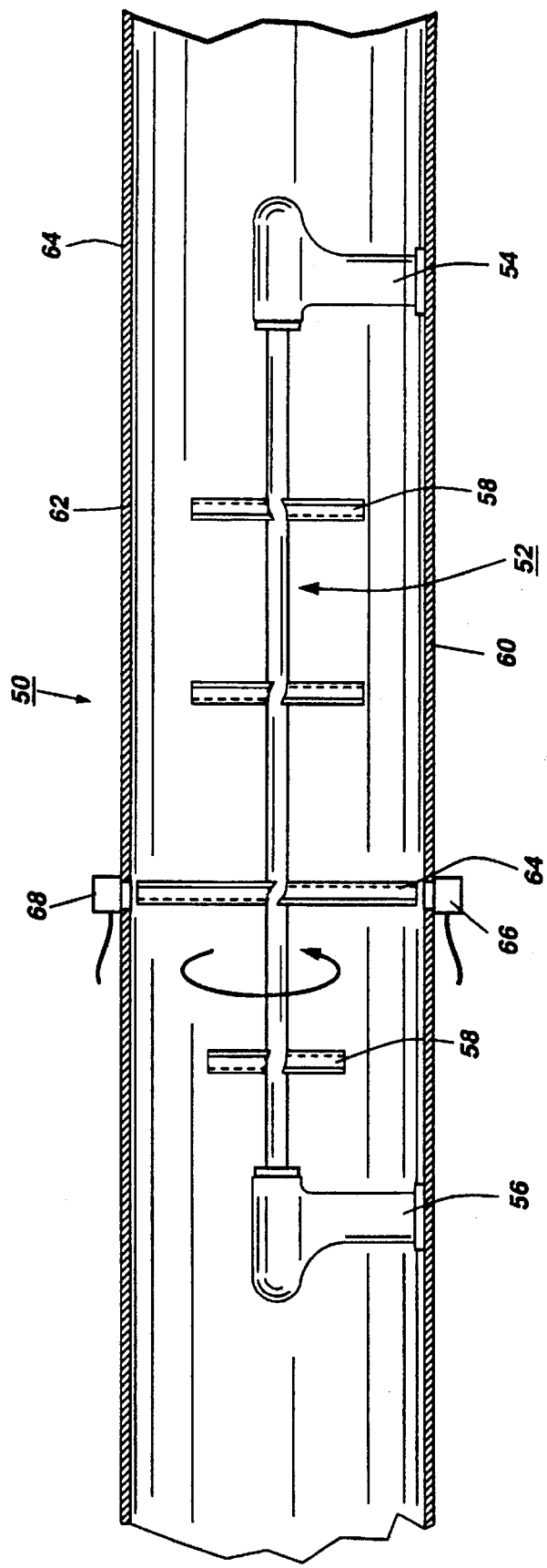
FIG. 2 is an elevational view, partially in section, showing another embodiment of a sensor in accordance with the present invention.

FIG. 2 shows an elevational view of another embodiment of the combined fluid flow rate and density sensor of the present invention. Sensor 50 is shown with an upper tube wall portion 62 and lower tube wall portion 60; shaft 52 is mounted on trailing shaft support 54 and leading shaft support 56. Fins 58 on shaft 52 cause shaft 52 to rotate in the direction indicated in response to the flow of fluid through sensor 50. As shaft 52 rotates, the ends of light pipe 64 moves past light emitter 66 and light detector 68 such that the flow rate and density of the fluid flowing through sensor 50 may be determined by a remote sensor or detector (not shown). Sensor 50 is shown in FIG. 2 using a single pipe 64 as shown; other single light pipe (FIG. 3C) or multiple light pipe (FIGS. 1, 3A or 5) configurations may also be used to detect flow rate and/or fluid characteristics.

Figure 3A:
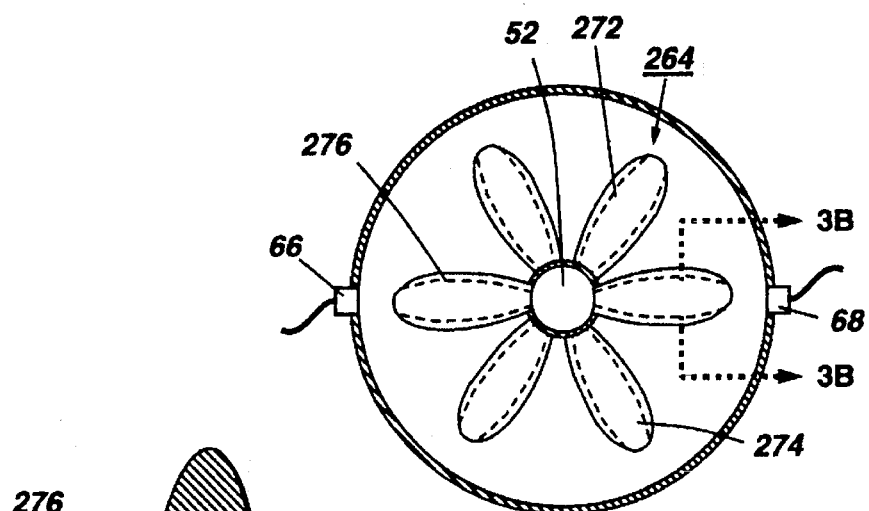
FIG. 3A is an elevational view, partially in section, showing a sensor in accordance with the present invention.
Figure 3B:
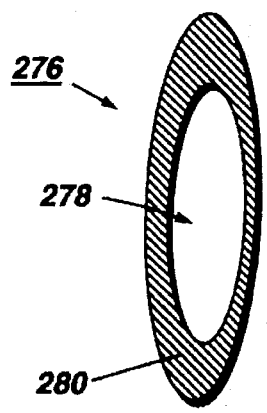
FIG. 3B is a sectional elevational view taken along the line in the direction of the arrow 3B of FIG. 3A.

FIG. 3A shows a 6 blade, 3 light pipe assembly. Blades 272, 274 and 276 are shown fixed on light transmissive shaft 52, so as to make up a 6 blade prop 264. An emitter 66 intermittently projects light through each of blades 272, 274 and 276 as they rotate past, such that detector 68 receives light as it passes through the transparent interior portion of each blade. FIG. 3B shows a cross-section of blade 276 taken in the direction of the arrows shown in FIG. 3A, in which a hollow or light transparent, translucent or otherwise transmissive portion 278 is surrounded by a opaque area 280. The 6 blade configuration of prop 264 as shown in FIGS. 3A and 3B permits accurate detection of slower moving fluid flows. The length of one (or more) blades of the sensor may vary as described in conjunction with FIG. 1, or may be the same.

Figure 3D:
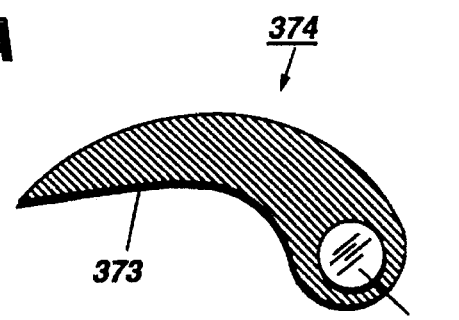
FIG. 3D is a sectional elevational view taken along the line in the direction of the arrow 3D of FIG. 3C.
Figure 3C:
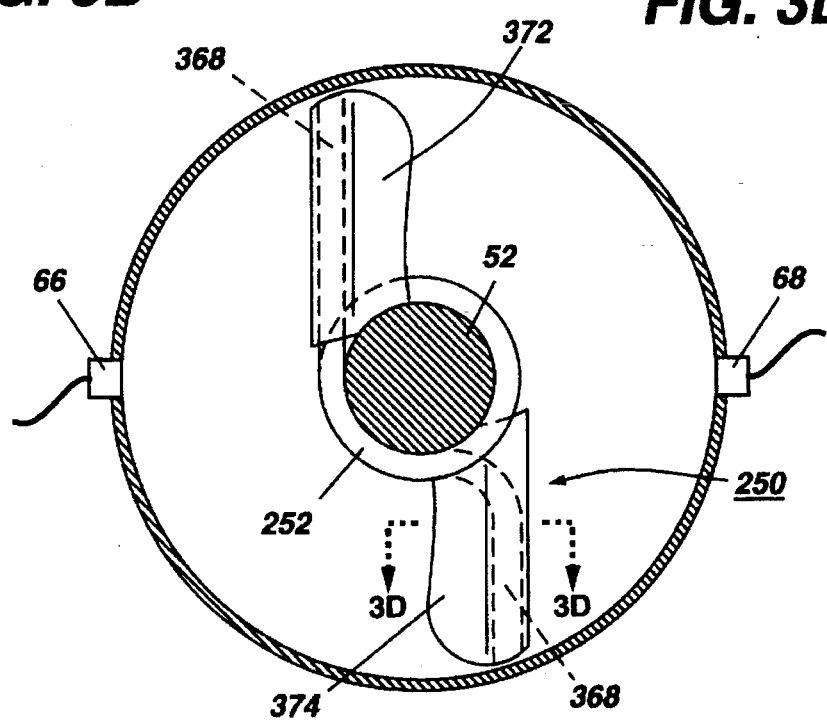
FIG. 3C is an elevational view, partially in section, showing a sensor in accordance with the present invention.

FIG. 3C shows another embodiment of a fluid flow sensor of the present invention. Blade members 372 and 376 are shown with a fiber optic member 368 extending therethrough. Each blade 372 and 374 is affixed to shaft 52 so as to form prop 250. As each light pipe 368 passes emitter 66, light is transmitted therethrough so as to be detected by detector 68. FIG. 3D shown a cross-sectional view of blade 374 of FIG. 3C taken in the direction of the arrows shown. Optic fiber 368 passes through the solid portion 373 of blade 374. The embodiment of the present invention shown in FIGS. 3C and 3D is well suited to rapid fluid flow, due to its fluid-dynamically formed blades 272 and 274.

Figure 4A:
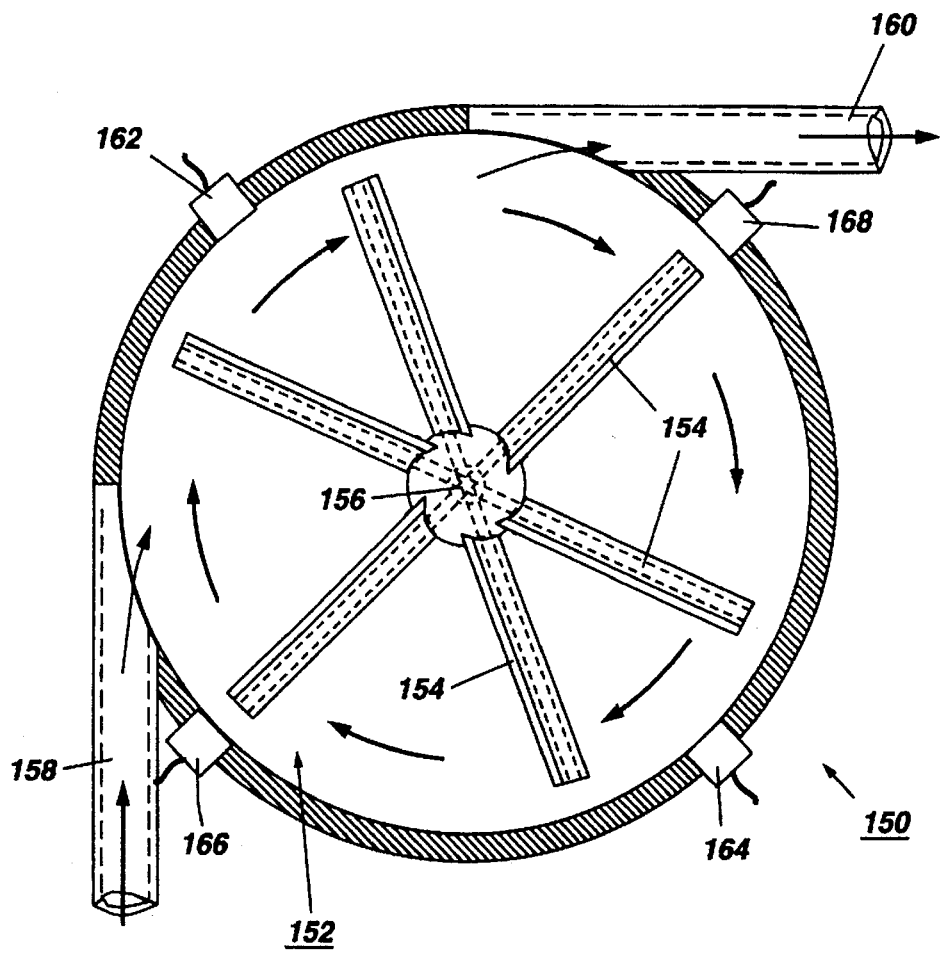
FIG. 4A is an elevational view, partially in section, showing another embodiment of a sensor of the present invention.
Figure 4B:
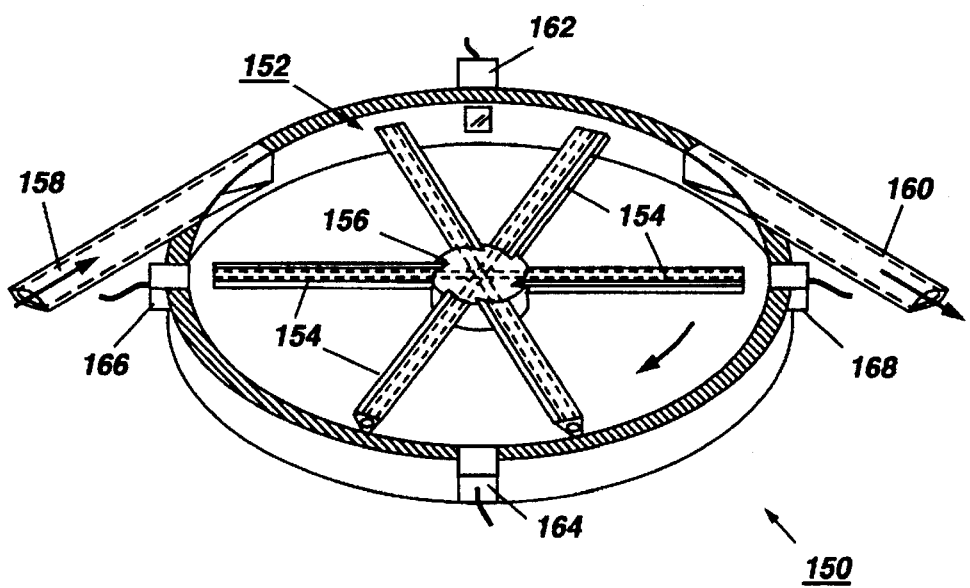
FIG. 4B is a perspective view, partially in section, showing a sensor arrangement shown in FIG. 4A.

FIG. 4A shows another embodiment of the flow sensor of the present invention. Blades 154 are mounted to a shaft 156 which rotates in flow sensor 150. Light emitters 162 and 166 emit light into the ends of blades 154 such that light can be detected and analyzed by light receptors 164 and 168. Fluid flows into the interior body area 152 of sensor 150 via conduit 158, where it causes blades 154 to rotate about pivot 156. Fluid is thereafter released from interior body area 152 from sensor 150 by conduit 160 in the direction of the arrow shown. FIG. 4B shows a perspective view of the flow sensor of the present invention, in which fluid flows into sensor 150 via conduit 158 in the direction of arrow shown. Fluid then circulates through the central body portion 152 in the direction the of arrow shown, exerting pressure on blades 154 so as to rotate them about pivot 156 in the direction of fluid flow. Fluid is thereafter released from sensor 150 by conduit 160 in the direction of the arrow shown.

FIG. 5 shows another embodiment of flow sensor 200 of the present invention. Shaft 202 is rotatably mounted in flow sensor 200 by brackets 204 and 206. Prop members 208 are positioned in a narrow portion of flow sensor 200; the positioning of props 208 in such a constricted flow zone of flow sensor 200 causes shaft 202 to rotate more rapidly according to the increased flow rate in this zone. The use of multiple props 208 rotates light pipes 210 and 211 past light emitter 214 and light detector 216 in even highly viscous fluids. As shaft 202 rotates, light pipes 210 and 211 rotate pass emitter 214 and detector 216, so as to permit flow rate sensing, particulate component detection, specular analysis and other sensing operations.

Figure 6:
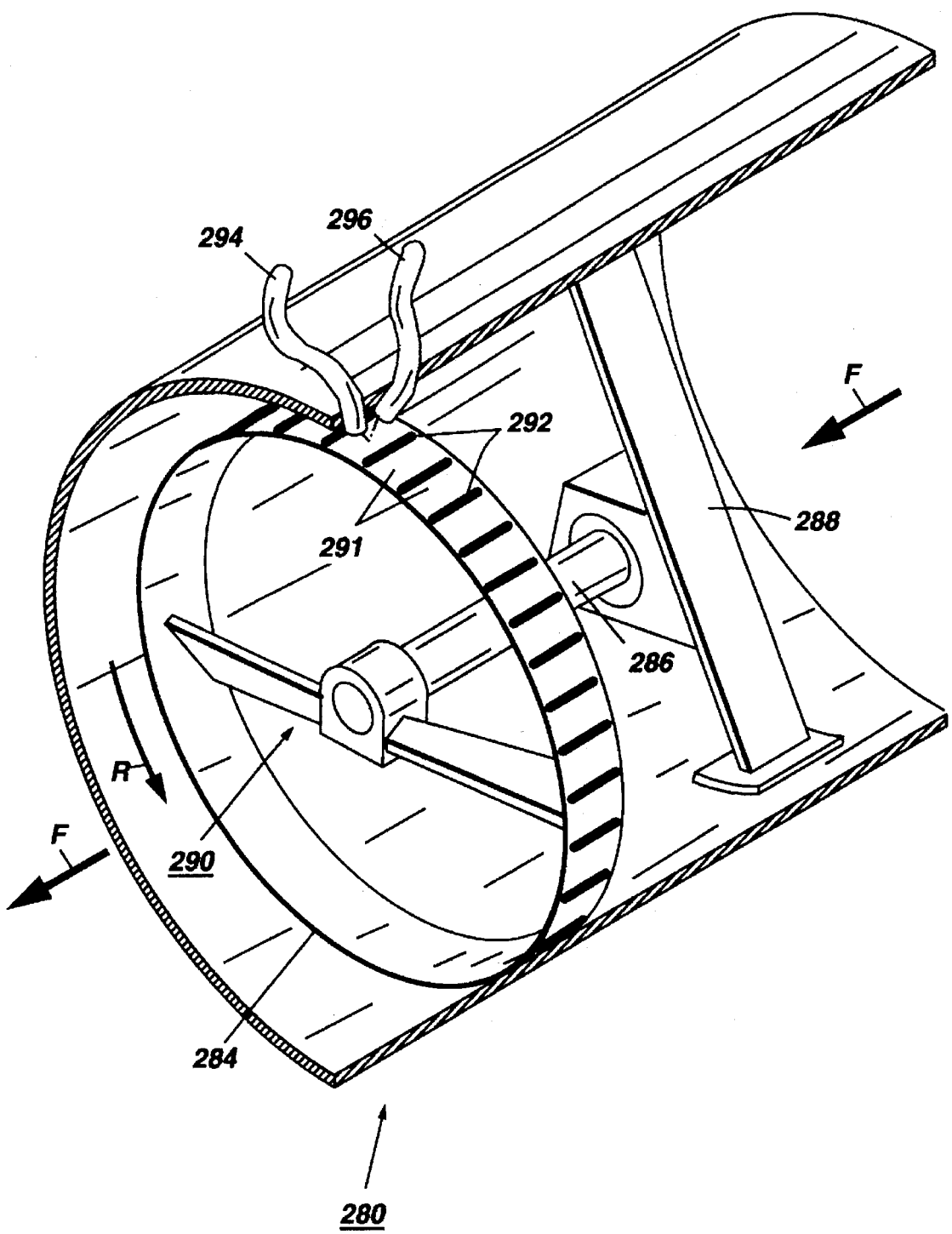
FIG. 6 is a perspective view, partially in section, showing another embodiment of a sensor of the present invention.

FIG. 6 shown another embodiment of the flow sensor 280 of the present invention. Shaft 286 of sensor 280 is rotatably mounted on support member 288; prop member 290 rotates in direction "R" according to fluid flow in direction "F" as shown. Ring 284 is attached as shown to the ends of prop 290, and includes on its outer circumference reflective areas 291 and nonreflective timing marks 292. Light from a remote light source (not shown) is emitted from emitter optic fiber 294 towards the circumference of ring 284. As ring 284 rotates with prop 290 in response to fluid flow, receptor optic fiber 296 transmits light reflected by reflective areas 291 from emitter optic fiber 294, and similarly, detects the appearance of timing marks 292. A remote sensor (not shown) evaluates the pulses of light provided by receptor optic fiber 296. Further, according to the frequency of timing marks 292, the flow rate of the fluid through sensor 280 is detected.

In alternative embodiments (not shown in FIG. 6), selected or alternating reflective areas 291 may be recessed into ring 284 such that the fluid gap through which light passes can be uniformly varied, such as with the multiple light pipes shown in FIG. 1 of the present invention. In another embodiment, timing marks 292 may be holes or apertures in ring 284 that do not reflect light from emitter optic fiber 294 to receptor optic fiber 296. As is also adaptable to other embodiments of the present invention such as those shown in FIGS. 1-5 and 7, emitter optic fiber 294 and receptor optic fiber 296 may direct light from the LED light, infrared, ultraviolet, white, spectral or other light source through the fluid. As shown in FIG. 6, sensor 280 precisely positions optic fiber 294 to direct columnated light towards photoreceptor ring 284. In alternative embodiments, blades (such shown in FIGS. 3A and 3C) may be equipped with reflective tip facets similar to reflective areas 291 shown in FIG. 6 to reflect light to receptor optic fiber 296.

Figure 7:
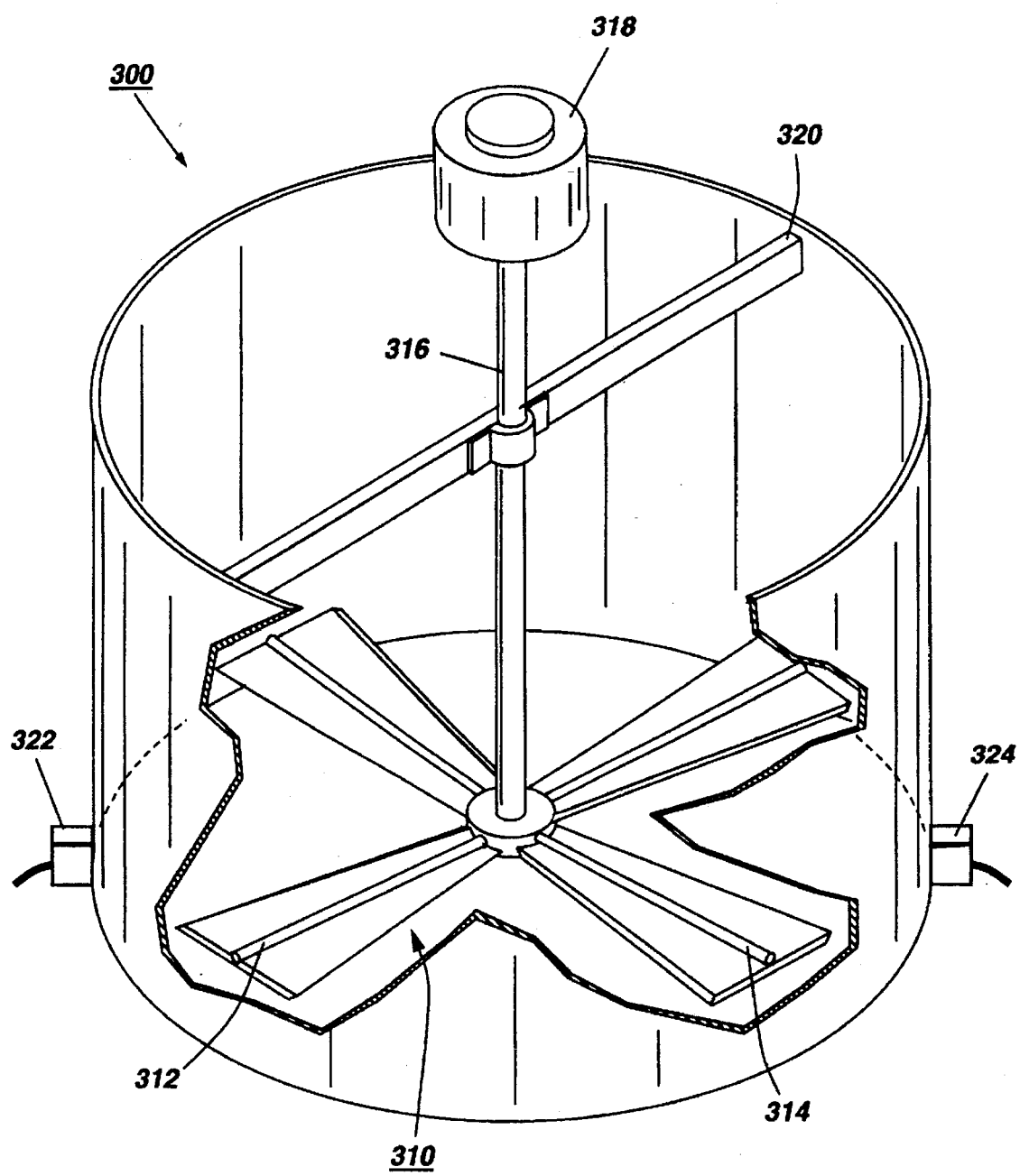
FIG. 7 is a perspective view, partially in section, showing another embodiment of a sensor of the present invention.

FIG. 7 shows another embodiment of the sensor/mixing chamber of the present invention. Sensor/mixing chamber 300 includes a mixing prop 310, with light pipes 312 and 314 extending therethrough. Prop 310 is mounted on shaft 316, rotatably held in position on support member 320. Shaft 316 is rotated by motor 318, which is fixed by supports (not shown) to sensor/mixing chamber 300. As the ends of light pipes 312 and 314 pass emitter 322 and detector 324, a variety of the attributes of the fluid being mixed by prop 310 can be evaluated, as previously described in association with FIG. 1. The sensors shown and described in conjunction with FIGS. 1-7 may be optically connected with fiber optic tubes to centralized and/or remote emitter and receptor assemblies capable of servicing a plurality of light emitters and receptors.

While the invention has been described in conjunction with a specific embodiment thereof, it is evident that many alternatives, modifications, and variations will be apparent to those skilled in the art. Accordingly, it is intended to embrace all such alternatives, modifications and variations that fall within the spirit and scope of the appended claims.

I claim:

1. An apparatus for sensing a fluid, comprising:

an emitter for projecting a light beam;

a detector for transmitting a signal in response to receiving the light beam;

a rotatable member for transmitting the beam of light from said emitter to said detector through a quantity of said fluid, said rotatable member further comprising a first light pipe having a first length and a second light pipe having a second length unequal to the first length, said first light pipe and said second light pipe alternately transmitting said light beam from said emitter to said detector according to rotation of of said rotatable member.

2. The apparatus of claim 1, further comprising a processor for determining a density of the fluid as a function of the signal from said detector.

3. The apparatus of claim 1, further comprising a processor for determining particulate concentrations in the fluid as a function of the signal from said detector.

4. The apparatus of claim 1, further comprising a processor for determining a flow rate of the fluid as a function of the signal from said detector.

5. The apparatus of claim 1, further comprising a processor, responsive to the signal from said detector, for determining a density and a flow rate of the fluid.

6. The apparatus of claim 1, wherein said rotatable member rotates in response to a flow of the fluid.

7. The apparatus of claim 1 wherein the light beam passes across a first distance of the fluid between said emitter and said first light pipe and across a second distance of the fluid between said emitter and said second light pipe.

8. The apparatus of claim 1, wherein the light beam passes across a first distance of the fluid between said first light pipe and said detector and across a second distance of the fluid between said second light pipe and said detector.

9. The apparatus of claim 8 wherein said first distance is unequal to said second distance.

10. The apparatus of claim 1, wherein said rotatable member comprises:

a blade for turning the rotatable member in response to a flow of fluid impacting thereon.

11. The apparatus of claim 10, wherein said blade mixes said fluid.

12. The apparatus of claim 1, wherein said rotatable member further comprises:

a first blade affixed to said rotable member, said first blade having the first light pipe extending therethrough for transmitting light from said emitter to said detector; and a second blade affixed to said rotable member, said second blade having the second light pipe extending therethrough for transmitting light from said emitter to said detector, said first and second blades operable to turn the rotatable member in response to a flow of fluid impacting thereon.

* * * * *